(12) United States Patent
Leibitzki et al.

(10) Patent No.: US 9,901,694 B2
(45) Date of Patent: Feb. 27, 2018

(54) NECK PATCH FOR TRACHEAL CANNULAS OR ARTIFICIAL NOSES HAVING A SPEAKING VALVE

(75) Inventors: Harry Leibitzki, Blankenburg (DE); Steffen Süβ, Halberstadt (DE)

(73) Assignee: Primed Halberstadt Medizintechnik GmbH, Halberstadt (DE)

( * ) Notice: Subject to any disclaimer, the term of this patent is extended or adjusted under 35 U.S.C. 154(b) by 801 days.

(21) Appl. No.: 13/879,975

(22) PCT Filed: Oct. 14, 2011

(86) PCT No.: PCT/DE2011/001867
§ 371 (c)(1),
(2), (4) Date: Apr. 24, 2013

(87) PCT Pub. No.: WO2012/055389
PCT Pub. Date: May 3, 2012

(65) Prior Publication Data
US 2013/0213404 A1   Aug. 22, 2013

(30) Foreign Application Priority Data
Oct. 29, 2010   (DE) .................. 10 2010 049 895

(51) Int. Cl.
*A61M 5/32*   (2006.01)
*A61M 16/04*   (2006.01)
*A61F 13/00*   (2006.01)

(52) U.S. Cl.
CPC ...... *A61M 16/047* (2013.01); *A61M 16/0468* (2013.01); *A61F 2013/00412* (2013.01)

(58) Field of Classification Search
CPC .. A61M 2025/0266; A61M 2025/0233; A61M 2025/022; A61M 16/047
(Continued)

(56) References Cited

U.S. PATENT DOCUMENTS 4,325,366 A * 4/1982 Tabor ................ A61M 16/0468
128/207.16
4,699,616 A * 10/1987 Nowak ................ A61M 25/02
128/DIG. 26
(Continued)

FOREIGN PATENT DOCUMENTS

DE   10392887   7/2005
DE   10 2005 055 331   10/2006
(Continued)

*Primary Examiner* — Edelmira Bosques
(74) *Attorney, Agent, or Firm* — Norris McLaughlin & Marcus, P.A.

(57) ABSTRACT

There is provided a neck patch to be adhered on a tracheostoma, which is very light and has a good respiratory activity and an excellent sealing behavior when adhered on top of a tracheostoma in the neck of a patient. The neck patch is made of a thin, planar, flexible foil having a thickness of between 5 and 30 μm, which is adhesive on its proximal side only and has a centrically arranged hole on its distal side, and around which a hard, round plastic connector disk having a central recess is arranged, the neck patch further comprising a supporting frame that surrounds the outer edge of the film and is approximately five to ten times thicker than the film so that the neck patch can be positioned without being rolled together.

6 Claims, 1 Drawing Sheet

(58) Field of Classification Search
USPC .......................................................... 604/180
See application file for complete search history.

(56) References Cited

U.S. PATENT DOCUMENTS

| | | | |
|---|---|---|---|
| 5,000,741 A | 3/1991 | Kalt | |
| 5,480,432 A * | 1/1996 | Suding | A61F 2/203 |
| | | | 128/207.16 |
| 5,738,095 A * | 4/1998 | Persson | A61F 2/20 |
| | | | 128/201.13 |
| 2007/0079831 A1 | 4/2007 | Worthington | |

FOREIGN PATENT DOCUMENTS

| | | |
|---|---|---|
| DE | 10-2005-055331 B3 | 10/2006 |
| WO | WO-90/06732 | 6/1990 |
| WO | Wo-91/05579 | 5/1991 |
| WO | WO-99/29268 | 6/1999 |
| WO | WO-2004/000401 | 12/2003 |
| WO | WO-2009/075636 | 6/2009 |

* cited by examiner

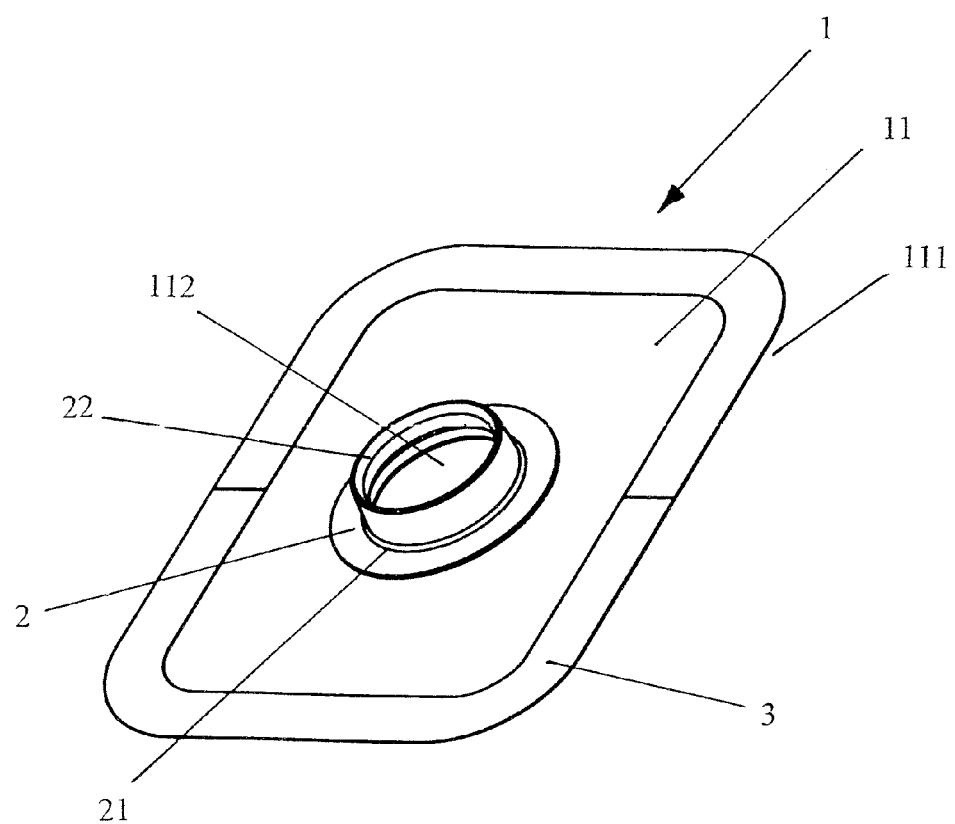

NECK PATCH FOR TRACHEAL CANNULAS OR ARTIFICIAL NOSES HAVING A SPEAKING VALVE

BACKGROUND OF THE INVENTION

The present invention relates to a neck patch for tracheal cannulas or artificial noses having a speaking valve, which is to be adhered on a tracheostoma.

Tracheostoma prostheses (also known as tracheal cannulas or tracheostoma tubes) for treating patients without larynx (laryngectomees) with opened throat (so called tracheostoma) have been known for decades. These prostheses are available with and without speaking valve. However, the different embodiments provided with a speaking valve have become more and more important in the rehabilitation of laryngectomees because they make speaking success possible for the patients.

The tracheostoma prostheses are inserted into a tracheostoma and fixed therein.

Securing straps and patches, for example, are used for fixing these prostheses on the outside at the patient's skin.

DE 10 392 887 T5 discloses a tracheal cannula fixation unit including a flat part, which comprises an opening for the insertion and simultaneous support of a tracheal cannula and a fixation surface provided with an adhesive gel material. The fixation surface is designed to retain the cannula in the tracheostoma and to provide a perfect sealing between the cannula and the tracheostoma.

DE 20 2008 017 105 U1 describes a tracheostoma stabilization unit that is used to support the fixation of cannulas, filters and valves on a stoma and is designed as a planar flat part provided with an opening, which is not used for securing the tracheal cannula, and said flat part of the stabilization unit to be adhered by an adhesive film on the skin surrounding the tracheostoma is designed as a soft and elastic element for the lateral sealing of the uneven areas.

This soft and elastic function under the adhesive film is generated by a circular foam material firmly bonded with a hard, round plastic disk.

The adhesive film above the hard plastic disk is designed as a patch comprising a holding ring for cannulas, valves, filters, etc. The patch can be bonded to the patient's skin.

According to DE 20 2008 017 105 U1 the flat part has a thickness of between 3 and 5 mm and the adhesive film is provided with an adhesive on both sides.

This technical solution has the disadvantage that the plastic disk is rather rigid and has not a respiratory activity and the foam material leads to an increased overall height of the unit so that the wearing comfort is not very good for the patient.

SUMMARY OF THE INVENTION

The aim of the invention is to provide a neck patch to be adhered on a tracheostoma, which is very light, has a good respiratory activity and an excellent sealing behavior when properly adhered on top of a tracheostoma in the neck of a patient.

Furthermore, the inventive unit shall have a low overall height that increases both the respiratory activity and the wearing comfort for the patient.

Said aim is achieved by a neck patch according to the first claim. Advantageous embodiments of this invention are specified in the sub-claims.

The nature of this invention is to provide a neck patch which is made of a thin, planar, flexible film having a thickness of between 5 and 30 µm, which is adhesive on its proximal side (the side facing the patient) only and has a centrically arranged hole on its distal side (the side facing away from the patient), around which a hard, round plastic disk having centrical recess, e.g., throughhole, is arranged, and said neck patch further comprises a supporting frame that surrounds the outer edge of the film and is approximately five to ten times thicker than the film so that the neck patch can be positioned without being rolled together, i.e., the film is retained in flat or planar form by the frame.

Advantageously, the film is an elastomer film, for example made of TPU (thermoplastic urethane) or TPE (thermoplastic polyethylene).

The film and the frame can be designed as a single part or as two parts with a rectangular or oval shape.

The plastic disk/the connector is made of a considerably harder plastic material than the one of the film and the frame, for example of silicone, PVU, PET, PU or PE or a metallic material, and functions as a screw, bayonet or clamp lock. Diverse components, such as tracheal cannulas, artificial noses, valves, etc., can be held by this lock.

The advantage of the inventive neck patch is the good respiratory activity and the excellent sealing behavior when the very thin film is properly adhered on a tracheostoma in the neck of a patient and the simultaneous good support of the parts at the plastic disk/the connector of the patch.

A special advantage is the fact that the inventive neck patch is not provided with a hard plastic disk with foam padding known from the state of the art so that the overall height (inventive neck patch+a further part, such as a very flat lateral nose having a height of 5 mm) can be kept very low and thus the respiratory activity and the wearing comfort for the patient are considerably increased.

The invention is explained in detail by means of the following embodiment and the FIGURE.

BRIEF DESCRIPTION OF THE DRAWINGS

The drawing is a schematic 3D view of an embodiment of the inventive neck patch.

DETAILED DESCRIPTION OF THE INVENTION

The drawing shows a neck patch (1) made of a thin, planar, flexible foil (11) having a thickness of between 5 and 30 µm, which is adhesive on its proximal side (the side facing the patient) only and has a centrically arranged hole (112) on its distal side (the side facing away from the patient), around said hole a hard, round plastic disk (2)/connector (2) having a central recess (21) is arranged, and said neck patch further comprises a supporting frame (3) that surrounds the outer edge of the film and is approximately five to ten times thicker than the film (11) so that the neck patch (1) can be positioned without being rolled together.

The film (11) is an elastomer film made of thermoplastic urethane.

The film (11) and the supporting frame (3) can be designed as a single part or as two parts.

The plastic disk (2)/connector (2) is made of silicone and is provided with a holding lock edge (22). A flat lateral artificial nose can be held by means of this plastic disk (2)/connector (2).

All features disclosed in the description, the embodiments and the subsequent claims can be important for the invention both individually and in any combination.

The invention claimed is:

1. A foam-free neck patch configured to be adhered directly on a tracheostoma, the neck patch consisting of a thin, planar, flexible film having a thickness of between 5 and 30 µm, which is adhesive on its proximal side only for adhering of the neck patch directly on the tracheostoma and having a centrically arranged hole and on its distal side, around the hole an annular hard, round plastic connector disk configured to lock a tracheal cannula, artificial nose or valve onto the neck patch, the proximal side of the neck patch being configured to face the tracheostoma and the distal side of the neck patch being configured to face away from the tracheostoma, and a supporting frame that surrounds outer edges of the film at an entire periphery of the film, is approximately five to ten times thicker than the film and is thus configured to support the film in a flat or planar form so that the neck patch can be positioned while the film is retained in a flat or planar form by the frame.

2. The neck patch configured to be adhered on a tracheostoma according to claim 1, wherein the film is an elastomer film made of a thermoplastic material.

3. The neck patch configured to be adhered on a tracheostoma according to claim 1, wherein the film and the supporting frame are a single part.

4. The neck patch configured to be adhered on a tracheostoma according to claim 1, wherein the connector disk is made of silicone and is provided with a holding lock edge.

5. The neck patch configured to be adhered on a tracheostoma according to claim 1, wherein the film and the supporting frame are each a respective part.

6. Method of fixing a tracheostoma prosthesis on a tracheostoma, comprising adhering a neck patch according to claim 1 on the tracheostoma with the centrically arranged hole of the neck patch aligned with the tracheostoma, and affixing the prosthesis to the connector disk of the neck patch.

* * * * *